United States Patent
Takeda et al.

(10) Patent No.: US 10,905,635 B2
(45) Date of Patent: *Feb. 2, 2021

(54) GAS-CONTAINING BASE MATERIAL AND MANUFACTURING METHOD THEREFOR

(71) Applicant: Shinryo Corporation, Kyushu (JP)

(72) Inventors: Tooru Takeda, Kyushu (JP); Hirokazu Toyoshima, Kyushu (JP); Takeshi Sawai, Kyushu (JP); Kazumi Inoue, Kyushu (JP)

(73) Assignee: Shinryo Corporation, Kita Kyushu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/149,449

(22) Filed: Oct. 2, 2018

(65) Prior Publication Data

US 2019/0029927 A1 Jan. 31, 2019

Related U.S. Application Data

(63) Continuation of application No. PCT/JP2017/014987, filed on Apr. 12, 2017.

(30) Foreign Application Priority Data

Apr. 14, 2016 (JP) .................... 2016-081449
Jan. 12, 2017 (JP) .................... 2017-003163

(51) Int. Cl.
*A61K 8/02* (2006.01)
*B01F 5/16* (2006.01)
(Continued)

(52) U.S. Cl.
CPC ............ *A61K 8/0204* (2013.01); *A23L 33/10* (2016.08); *A23P 30/40* (2016.08); *A61K 8/19* (2013.01);
(Continued)

(58) Field of Classification Search
CPC . A61K 47/36; A61K 8/73; A61K 8/65; A61K 9/0087; A23L 33/10; B01F 5/16; A23P 30/40; A23V 2002/00
See application file for complete search history.

(56) References Cited

U.S. PATENT DOCUMENTS

2014/0370096 A1  12/2014  Eckert

FOREIGN PATENT DOCUMENTS

CN   101204205 A   6/2008
CN   101489416     7/2009
(Continued)

OTHER PUBLICATIONS

Japanese Office Action dated Jun. 25, 2019, in Patent Application No. 2018-155689, 6 pages (with English translation).
(Continued)

*Primary Examiner* — Jianfeng Song
(74) *Attorney, Agent, or Firm* — Oblon, McClelland, Maier & Neustadt, L.L.P.

(57) ABSTRACT

A gas-containing base material including a functional-gas-containing composition, where the composition is a gel-like composition having a gelation temperature in a range of 0.5° C. or higher and 65° C. or lower at which a liquid form is able to be changed to a solid form by cooling, and where the composition contains an amount of a bubble state functional gas which exceeds a saturated solubility when the composition is in a liquid form.

4 Claims, 4 Drawing Sheets

(51) Int. Cl.
| | |
|---|---|
| *B01F 5/06* | (2006.01) |
| *A23L 33/10* | (2016.01) |
| *A61K 9/00* | (2006.01) |
| *A61K 47/42* | (2017.01) |
| *A61K 47/02* | (2006.01) |
| *A61K 47/36* | (2006.01) |
| *A61K 8/19* | (2006.01) |
| *A61K 8/73* | (2006.01) |
| *A61K 8/65* | (2006.01) |
| *B01J 13/00* | (2006.01) |
| *A23P 30/40* | (2016.01) |
| *A61Q 19/00* | (2006.01) |

(52) U.S. Cl.
CPC ............... *A61K 8/65* (2013.01); *A61K 8/73* (2013.01); *A61K 9/0087* (2013.01); *A61K 47/02* (2013.01); *A61K 47/36* (2013.01); *A61K 47/42* (2013.01); *B01F 5/0602* (2013.01); *B01F 5/16* (2013.01); *B01J 13/0065* (2013.01); *A23V 2002/00* (2013.01); *A61Q 19/00* (2013.01)

(56) References Cited

FOREIGN PATENT DOCUMENTS

| | | | |
|---|---|---|---|
| CN | 103987269 A | | 8/2014 |
| EP | 2465358 A1 | | 6/2012 |
| JP | 54-154385 U | | 10/1979 |
| JP | 59-51748 | | 3/1984 |
| JP | 3106002 U | * | 12/2004 |
| JP | 3106002 U | | 12/2004 |
| JP | 2007-314496 | | 12/2007 |
| JP | 4450863 | | 4/2010 |
| JP | 4600889 | | 12/2010 |
| JP | 2012-147757 | | 8/2012 |
| JP | 2012147757 | * | 8/2012 |
| JP | 2014-213064 | | 11/2014 |
| JP | 2016-13547 A | | 1/2016 |
| WO | WO 2012/033895 A2 | | 3/2012 |

OTHER PUBLICATIONS

International Search Report dated May 30, 2017 in PCT/JP2017/014987, filed on Apr. 12, 2017 (with English Translation).

Office Action dated Sep. 22, 2020, in corresponding Chinese Patent Application No. 201780023001.X (with partial English translation), citing documents AO to AS therein.

* cited by examiner

RAW MATERIAL COMPOSITION
(GELATIN AQUEOUS SOLUTION)
WITH GELATIN CONCENTRATION OF 35 wt%

HYDROGEN GAS-CONTAINING
BASE MATERIAL

RAW MATERIAL COMPOSITION
(GELATIN AQUEOUS SOLUTION)
WITH GELATIN CONCENTRATION OF 35 wt%

AIR-CONTAINING
BASE MATERIAL

FIG. 7

GAS-CONTAINING BASE MATERIAL AND MANUFACTURING METHOD THEREFOR

The present application is a continuation application of International Application No. PCT/JP2017/014987, filed on Apr. 12, 2017, which claims priority of Japanese Patent Application No. 2016-081449, filed Apr. 14, 2016, and Japanese Patent Application No. 2017-003163, filed Jan. 12, 2017, the contents of which are incorporated herein by reference.

TECHNICAL FIELD

The present invention relates to a gas-containing base material containing a functional gas such as hydrogen gas, oxygen gas, nitrogen gas, and carbon dioxide gas with a high concentration which are valuable in industrial fields such as foods, cosmetics, medicine, and cell culture, and a method of producing the same.

BACKGROUND ART

Dissolving or dispersing a functional gas having an antioxidant effect for a living body such as hydrogen gas in an aqueous solution or a jelly, and processing it into a liquid form, a jelly form, a sheet form, or a capsule form has been proposed, and the processed form is useful for cosmetics, foods, and pharmaceuticals.

For example, Patent Document 1 describes a method of producing a cosmetic liquid obtained by blowing pressurized hydrogen gas into purified water to generate microbubbles, producing hydrogen-containing water with a dissolved hydrogen concentration of 0.5 to 1.5 ppm, and adding a moisturizing agent and the like thereto. In addition, Patent Document 2 describes a method in which hydrogen gas is blown into water or a low viscosity liquid to generate fine hydrogen gas bubbles, this liquid is transferred to another adjacent tank, a gelling agent is added thereto, and a gelled functional jelly containing hydrogen gas is produced.

In addition, Patent Document 3 describes a sheet for skin obtained by generating a sheet-like holding layer containing dissolved hydrogen gas according to the method described in Patent Document 1, and laminating a hydrogen reflective layer using a hydrogen barrier material on one side thereof.

CITATION LIST

Patent Literature

[Patent Document 1]
Japanese Patent No. 4600889
[Patent Document 2]
Japanese Patent No. 4450863
[Patent Document 3]
Japanese Unexamined Patent Application, First Publication No. 2014-213064

SUMMARY OF INVENTION

Technical Problem

However, Patent Document 1 provides a method of producing a cosmetic liquid including a hydrogen-containing water producing process in which, after hydrogen gas is blown into purified water at a gas pressure of 0.25 MPa and a gas flow rate of 0.1 to 1 L/min, hydrogen gas ejected from a porous element with a pore size of 2 to 120 μm becomes microbubbles, and hydrogen-containing water having a redox potential of −400 mV or lower, and an amount of a dissolved hydrogen gas of 0.5 to 1.5 ppm is produced, an aqueous phase production process in which a moisturizing agent is added to the hydrogen-containing water and dissolved to produce an aqueous phase, a non-aqueous phase production process in which a moisturizing agent is mixed in and dissolved and the hydrogen-containing water is added thereto to produce a non-aqueous phase separately from the aqueous phase production process, and a process of mixing the aqueous phase and the non-aqueous phase. However, since the obtained cosmetic liquid is in a liquid form, even if an amount of dissolved hydrogen gas is large, the amount does not reach 1.6 ppm or more of the saturated solubility.

In addition, in Patent Document 2, Patent Document 1 is cited as reference technical background. In the method, since hydrogen gas bubbles (microbubbles) disclosed in Patent Document 1 are unlikely to remain in a final product due to scattering, hydrogen gas is blown into water or a low viscosity liquid to generate fine hydrogen nanobubbles, this liquid is transferred to another adjacent tank, a gelling agent is added thereto, and a gelled functional jelly containing hydrogen gas is produced. However, in this specification, there is no description regarding the amount of hydrogen gas in the obtained product (functional jelly), and it is unknown whether hydrogen gas can be included at a higher concentration than that in Patent Document 1 according to the effect obtained when hydrogen nanobubbles are used.

Patent Document 3 describes a sheet for skin obtained by generating a sheet-like holding layer containing dissolved hydrogen gas according to the method described in Patent Document 1, and laminating a hydrogen reflective layer using a hydrogen barrier material on one side thereof. However, in this specification, only a preferable hydrogen concentration in the sheet-like holding layer of 0.8 mM (1.6 ppm) or more and 2.0 mM (4 ppm) or less is described, and there is no description regarding a specific production procedure of a hydrogen holding sheet and no examples are provided. Therefore, a hydrogen content in the final product when the method described in Patent Document 1 is used is considered to have a limit of 1.6 ppm even if the content is high.

As described above, in the related art, a material which contains an amount of hydrogen gas which exceeds a saturated solubility of 1.6 ppm (1.7 vol %) in the final product and which can contain and retain hydrogen gas with a high concentration has yet to be found. The development of a material that can contain and retain a functional gas such as hydrogen gas with a high concentration is desired.

Therefore, in a conventional material containing a functional gas such as hydrogen gas, there is insufficient functional gas that can be released to the atmosphere, and a beneficial effect of the functional gas cannot be sufficiently exhibited, and thus there is room for improvement.

Solution to Problem

Under such circumstances, an object of the present invention is to provide a gas-containing base material that can contain and retain a functional gas with a high concentration and a method of producing the same.

In order to solve the above problems, the inventors conducted extensive studies and as a result, found that the following inventions satisfy the above object and completed the present invention.

That is, the present invention relates to the following inventions.

<1> A gas-containing base material including a functional-gas-containing composition, wherein the composition is a gel-like composition having a gelation temperature in a range of 0.5° C. or higher and 65° C. or lower at which a liquid form is able to be changed to a solid form by cooling, and wherein the composition contains an amount of a bubble state functional gas which exceeds a saturated solubility when the composition is in a liquid form.

<2> The gas-containing base material according to <1>, wherein the functional gas is any one of the group consisting of hydrogen gas, oxygen gas, nitrogen gas, argon gas, helium gas, carbon dioxide gas, methane gas, ethane gas, propane gas, butane gas, and a mixed gas of two or more thereof.

<3> The gas-containing base material according to <1> or <2>, wherein the amount of the functional gas is 2 vol % or more and 60 vol % or less in terms of volume/weight % (v/w %) in the composition.

<4> The gas-containing base material according to <3>, wherein the functional gas is hydrogen gas.

<5> The gas-containing base material according to any one of <1> to <4>, wherein, when the composition is in a solid form, a bubble diameter of the contained functional gas is in a range of 1 μm or more and 200 μm or less.

<6> The gas-containing base material according to any one of <1> to <5>, wherein a gelation temperature of the composition is 10° C. or higher and 60° C. or lower.

<7> The gas-containing base material according to any one of <1> to <6>, wherein the composition includes at least one of the group consisting of gelatin, agar, carrageenan, pectin, glucomannan, pullulan and sodium alginate.

<8> The gas-containing base material according to any one of <1> to <7>, wherein the composition includes an additive.

<9> A method of producing a gas-containing base material including a functional-gas-containing composition, including the following processes:

Process (1): in this process, a functional gas is supplied to a raw material composition having a gelation temperature in a range of 0.5° C. or higher and 65° C. or lower at which a liquid form is able to be changed to a solid form by cooling while the temperature is maintained at a degree at which the raw material composition is in a liquid form, and an amount of the functional gas which exceeds a saturated solubility when the raw material composition is in a liquid form is uniformly dispersed as fine bubbles;

Process (2): in this process, the liquid raw material composition in which fine bubbles of the obtained functional gas are dispersed is transferred into a filling container and the filling container is filled and sealed; and Process (3): in this process, the liquid raw material composition in which the obtained fine functional gas bubbles in the sealed filling container are dispersed is cooled at a temperature equal to or lower than the gelation temperature of the raw material composition and solidified.

<10> The method of producing a gas-containing base material according to <9>, wherein, in Process (1), while the liquid raw material composition is stirred, a functional gas is supplied to the raw material composition, and the functional gas in the raw material composition is uniformly dispersed as fine bubbles.

<11> The method of producing a gas-containing base material according to <9>, wherein, in Process (1), without stirring the liquid raw material composition, after a functional gas is supplied to the raw material composition, the functional gas is uniformly dispersed as fine bubbles in the raw material composition according to shaking.

<12> The method of producing a gas-containing base material according to <9>, wherein, in Process (1), the liquid raw material composition and the functional gas are supplied to a line mixer, and the functional gas is uniformly dispersed as fine bubbles in the raw material composition.

<13> The method of producing a gas-containing base material according to any one of <9> to <12>, wherein, in Process (2), the liquid raw material composition is gradually cooled and transferred to the filling container while the temperature is maintained at a temperature of 5° C. or higher and 20° C. or lower, higher than the gelation temperature of the raw material composition.

<14> The method of producing a gas-containing base material according to any one of <9> to <13>, wherein the functional gas is any one of the group consisting of hydrogen gas, oxygen gas, nitrogen gas, argon gas, helium gas, carbon dioxide gas, methane gas, ethane gas, propane gas, butane gas and a mixed gas of two or more thereof.

<15> The method of producing a gas-containing base material according to any one of <9> to <14>, wherein the raw material composition includes at least one of the group consisting of gelatin, agar, carrageenan, pectin, glucomannan, pullulan and sodium alginate.

<16> The method of producing a gas-containing base material according to any one of <9> to <15>, wherein the raw material composition contains an additive.

Advantageous Effects of Invention

According to the present invention, there is provided a gas-containing base material that can contain and retain a functional gas with a high concentration. The gas-containing base material can release more functional gases into the atmosphere. In addition, according to the production method of the present invention, the functional gas can be included and retained at a high concentration in the gas-containing base material.

DESCRIPTION OF EMBODIMENTS

While embodiments of the present invention will be described below in detail, constituent features described below are only examples (representative examples) of embodiments of the present invention, and the present invention is not limited to any of the following details unless changing them would change the scope and spirit of the invention.

The present invention relates to a gas-containing base material including a functional-gas-containing composition (hereinafter referred to as a "gas-containing base material of the present invention" in some cases). The composition is a gel-like composition having a gelation temperature in a range of 0.5° C. or higher and 65° C. or lower at which a liquid form is able to be changed to a solid form by cooling. The composition includes an amount of a bubble state functional gas which exceeds a saturated solubility when the composition is in a liquid form.

Here, the gas-containing base material of the present invention can be suitably produced by a production method of the present invention to be described below.

The gas-containing base material of the present invention includes a composition (hereinafter referred to as a "composition of the present invention") having a gelation temperature in a range of 0.5° C. or higher and 65° C. or lower at which a liquid form can be changed to a solid form by cooling.

The gelation temperature of the composition of the present invention can be obtained by the method to be described below in examples.

Since the composition of the present invention has a gelation temperature in a range of 0.5° C. or higher and 65° C. or lower, the composition is in a solid form (gel state) at a temperature equal to or lower than the gelation temperature, and the composition in a solid form can contain bubble state functional gases. Here, the composition of the present invention is generally in a liquid form at a temperature equal to or higher than the gelation temperature.

The gas-containing base material of the present invention may include only the composition of the present invention or may include the composition of the present invention and other members.

For example, a component in which an arbitrary filler is dispersed in the composition of the present invention, a component in which the composition of the present invention is supported on an arbitrary carrier, or the like may be included in the gas-containing base material of the present invention.

The gas-containing base material of the present invention has an advantage that the contained composition of the present invention contains an amount of a bubble state functional gas which exceeds a saturated solubility when the composition is in a liquid form.

Here, the "saturated solubility (of a composition) in a liquid form" is a saturated solubility of the composition of the present invention in a liquid form under atmospheric pressure. Here, "dissolution of a gas" which defines a saturated solubility is determined by Henry's law and refers to a state in which a gas is dissolved in a molecular form according to a pressure.

Since the composition of the present invention contains a bubble state functional gas, it includes an amount of the functional gas which exceeds the saturated solubility.

Here, regarding the temperature at which the saturated solubility is measured, the composition of the present invention needs to be in a liquid form, and the temperature depends on components included in the composition of the present invention, but generally the saturated solubility may be measured at a temperature of 5° C. or higher and 10° C. or lower, higher than the gelation temperature.

The gas-containing base material of the present invention will be described below in further detail.

<Functional Gas>

The "functional gas" in the present invention is not particularly limited as long as it is a gas that can exhibit a beneficial function in the fields of foods, cosmetics, medicine, cell culture, and the like.

The functional gas can be used by being selected appropriately according to usage applications thereof. For example, hydrogen gas, oxygen gas, nitrogen gas, argon gas, helium gas, carbon dioxide gas, methane gas, ethane gas, propane gas and butane gas may be used alone or a mixed gas of two or more thereof may be used. Proportions of gases in the mixed gas are arbitrary. In addition, air is also included as the mixed gas.

Examples of a suitable functional gas include hydrogen gas, oxygen gas, nitrogen gas, argon gas, helium gas, and carbon dioxide gas.

As the functional gas, hydrogen gas is used in fields utilizing potential reduction and antioxidation such as foods, health foods, cosmetic medicine, and the like. In addition, oxygen gas is used in the fields of medicine, cell culture, health medical devices, and the like. In addition, since nitrogen gas, argon gas, and helium gas are inert gases due to their properties, use in the fields of foods, cosmetics, cell culture, and the like may be conceived in order to prevent oxidation. In addition, carbon dioxide gas is used in the fields of foods, cosmetics, and cell culture.

Among these, since hydrogen gas is a beneficial functional gas as described above, it is particularly suitable. Here, although it is difficult to incorporate hydrogen gas with a high concentration into a gel-like composition, a bubble state functional gas in a solid form can be included at a high concentration according to a production method of the present invention to be described below.

The amount of the functional gas in the gas-containing base material of the present invention can be appropriately selected according to the type of the gas and usage applications of the gas-containing base material of the present invention within a range in which the composition of the present invention can be retained.

The amount of the functional gas in the composition of the present invention can be obtained by a specific gravity method or a GC analysis to be described below in examples.

The amount of the functional gas in the composition of the present invention is preferably 2 vol % or more and 60 vol % or less, and more preferably 6 vol % or more and 60 vol % or less in terms of volume/weight % (v/w %) in the composition of the present invention. When the amount of the functional gas in the composition of the present invention is 2 vol % or more and 60 vol % or less in terms of volume/weight % (v/w %) in the composition of the present invention, gas bubbles with a high concentration can be uniformly and stably retained in the base material. In addition, since a moderate strength for the gas-containing base material can be maintained, it is possible to prevent shape collapse during storage. Here, the amount of the gas is a value obtained by sampling the composition of the present invention under conditions of atmospheric pressure and 10° C. according to a GC analysis method.

A bubble diameter of the contained functional gas when the composition of the present invention is in a solid form (gel state) is preferably in a range of 1 μm or more and 200 μm or less. If a bubble diameter of the contained functional gas when the composition is in a solid form (gel state) is in a range of 1 μm or more and 200 μm or less, gas bubbles can be uniformly dispersed in the base material. In addition, when gas bubbles are dispersed in the base material, since a rate at which gas bubbles rise due to buoyancy can be reduced, gas bubbles with a high concentration can be incorporated into the base material. A bubble diameter of a gas can be obtained by observing a cross section of the base material using, for example, a microscope (digital microscope VHX-900F commercially available from Keyence Corporation).

Here, a content and a bubble diameter of gases that can be retained in the composition of the present invention can be substantially determined by a method in which functional gas bubbles are dispersed in components of the composition and a liquid raw material composition.

<Composition of the Present Invention>

The composition of the present invention is a gel-like material which has a gelation temperature in a range of 0.5° C. or higher and 65° C. or lower at which a liquid form can be changed to a solid form by cooling as described above and in which fine functional gas bubbles can be dispersed and retained. The gelation temperature is preferably in a range of 0.5° C. or higher and 65° C. or lower because then gas bubbles can be stably retained in the base material during cold storage or room temperature storage in a high temperature area.

The composition of the present invention may be selected appropriately from a material group having the above gelation temperature and functional gas holding power according to usage applications of the gas-containing base material of the present invention. When the gas-containing base material of the present invention is used in the field of foods, cosmetics, medicine, cell culture, and the like, it may be selected appropriately in consideration of safety of the composition of the present invention (and other components) in a living body and adverse effects on cells during cell culture in addition to functional gas holding performance, storage stability, and a gelation temperature of the composition of the present invention, and is not limited to a specific material.

The composition of the present invention may be appropriately selected according to usage applications of the gas-containing base material of the present invention and a composition having a gelation temperature of 10° C. or higher and 60° C. or lower is preferable.

The composition of the present invention is a gel-like composition having a gelation temperature under atmospheric pressure and a temperature of 0.5° C. or higher and 65° C. or lower. Particularly, a gel-like composition that allows a reversible sol-gel transition at a gelation temperature is more preferable. Here, the gel-like composition includes a gelling component and water or an organic solvent.

Examples of the gelling component include proteins derived from natural products such as gelatin, agar, carrageenan, pectin, glucomannan, pullulan, sodium alginate, Aureobasidium broth, succinoglycan, americide gum, gum arabic, arabinogalactan, welan gum, cassia gum, gum ghatti, curdlan, karaya gum, carob bean gum, xanthan gum, chitosan, guar gum, guar gum enzymatic decomposition products, yeast cell walls, psyllium seed gum, Artemisia sphaerocephala seed gum, gellan gum, tamarind seed gum, tara gum, dextran, tragacanth gum, Abelmoschus manihot, microfibrous cellulose, furcelleran, fukuronori extracts, macrophomopsis gum, rhamsan gum, levan, okra extracts, seaweed cellulose, kelp extracts, konjac extracts, sweet-potato cellulose, soybean polysaccharides, and nata de coco and solid materials such as polysaccharides, synthetic organic polymers, and silicone type polymers. These materials may be used alone or two or more thereof may be used in combination.

Among these, the composition is preferably a composition including at least one of the group consisting of gelatin, agar, carrageenan, pectin, glucomannan, pullulan and sodium alginate as a gelling component.

The solvent is appropriately selected according to usage applications of the gas-containing base material of the present invention and the type of a component (particularly, a gelling component) of the composition of the present invention. For example, water, ethanol, and the like are used in the fields of foods, cosmetics, medicine, cell culture, and the like. An arbitrary organic solvent may be used in usage applications for which safety for humans is not required.

<Additives>

In addition, the composition of the present invention may appropriately contain optional additives in addition to the above material as long as the object of the present invention is not inhibited. As additives that can be added to the composition of the present invention, any known component can be used as long as it is a component that can be used in combination with the base material in order to exhibit a synergistic effect with its efficacy or impart new efficacy when the gas-containing base material of the present invention is used in the fields of foods, cosmetics, medicine, cell culture, and the like. While additives will be exemplified below, the present invention is not limited thereto.

Examples of the additives include a food additive, a cosmetic additive, an antioxidant, a medium additive, and a feed additive. For example, a fungicide such as sodium hypochlorite, sodium sulfite, or a high-degree bleaching powder, an emulsifier such as a glycerin fatty acid ester, a sucrose fatty acid ester, calcium stearyloyl lactate, a sorbitan fatty acid ester, or a propylene glycol fatty acid ester, a thickening stabilizer such as sodium alginate, a propylene glycol alginate ester, sodium propoxymethylcellulose, calcium propoxymethylcellulose, sodium starch glycolate, sodium polyacrylate, methylcellulose, hydroxymethylcellulose, or natural product polysaccharides, a water retention emulsion stabilizer such as sodium chondroitin sulfate, a binding agent and a quality modifier such as potassium polyphosphate, sodium polyphosphate, potassium metaphosphate, or sodium metaphosphate, an adhesion-preventing agent such as D-mannitol, a preservative such as benzoic acid and salts thereof, sorbic acid and salts thereof, paraoxybenzoic acid esters, sodium dehydroxyacetate, propionic acid and salts thereof, milt protein, polylysine, or a pectin decomposition product, an oxidation preventing agent such as erythorbic acid and salts thereof, isopropyl citrate, dibutylhydroxytoluene, dl-α tocopherol, nordihydroguaiaretic acid, butylated hydroxyanisole, or propyl gallate, and a reinforcing agent such as various types of vitamins may be exemplified. In addition, various amino acid derivatives, nucleic acids, lipids, antioxidants, anti-glycation agents, oils and fats, and surfactants known in the field can be used as additives.

Preferably, such additives are used alone or two or more types thereof may be used in combination depending on desired efficacy.

<Method of Producing a Gas-Containing Base Material>

In addition, the present invention relates to a method of producing a gas-containing base material. The method of producing a gas-containing base material (hereinafter referred to as a "production method of the present invention" in some cases) of the present invention includes the following processes.

Process (1):

In this process, a functional gas is supplied to a raw material composition having a gelation temperature in a range of 0.5° C. or higher and 65° C. or lower at which a liquid form is able to be changed to a solid form by cooling while the temperature is maintained at a degree at which the raw material composition is in a liquid form, and the amount of the functional gas which exceeds a saturated solubility when the raw material composition is in a liquid form is uniformly dispersed as fine bubbles.

Process (2):

In this process, the liquid raw material composition in which fine bubbles of the obtained functional gas are dispersed is transferred into a filling container and the filling container is filled and sealed.

Process (3):

In this process, the liquid raw material composition in which the obtained fine functional gas bubbles in the sealed filling container are dispersed is cooled at a temperature equal to or lower than the gelation temperature of the raw material composition and solidified.

The production method of the present invention is a suitable method of producing the above gas-containing base material of the present invention. According to the production method, it is possible to stably produce a gas-containing base material including a composition containing a functional gas with a high concentration.

In general, the functional gas is likely to move in the raw material composition and is likely to be dispersed as fine bubbles when a liquid viscosity of the liquid raw material composition when the gas-containing base material is produced is lower. However, when it is said that it is likely to move in the raw material composition, this means that it is unlikely to remain in the liquid raw material composition and it is highly likely to be vaporized into a gas phase. On the other hand, when a liquid viscosity of the liquid raw material composition when the gas-containing base material is produced is higher, the functional gas is unlikely to be dispersed and it is not preferable for fine bubbles to be formed. Needless to say, in a solid form in which the raw material composition is solidified, dispersion of the functional gas is not practically possible. In the production method of the present invention, after the functional gas with a high concentration is uniformly dispersed as fine bubbles in the liquid raw material composition, when cooling is quickly performed and the liquid raw material composition is solidified, fine functional gas bubbles can be included and retained at a high concentration.

<Process (1)>

Process (1) is a process in which a functional gas is supplied to a raw material composition having a gelation temperature in a range of 0.5° C. or higher and 65° C. or lower at which a liquid form is able to be changed to a solid form by cooling while the temperature is maintained at a degree at which the raw material composition is in a liquid form (a solution or a sol), and an amount of the functional gas which exceeds a saturated solubility when the raw material composition is in a liquid form is uniformly dispersed as fine bubbles.

The raw material composition before fine bubbles are dispersed used in Process (1) can be appropriately selected according to usage applications of the obtained gas-containing base material, but the above gelling component can be used.

Examples of the gelling component include proteins derived from natural products such as gelatin, agar, carrageenan, pectin, glucomannan, pullulan, sodium alginate, Aureobasidium broth, succinoglycan, americide gum, gum arabic, arabinogalactan, welan gum, cassia gum, gum ghatti, curdlan, karaya gum, carob bean gum, xanthan gum, chitosan, guar gum, guar gum enzymatic decomposition products, yeast cell walls, psyllium seed gum, Artemisia sphaerocephala seed gum, gellan gum, tamarind seed gum, tara gum, dextran, tragacanth gum, Abelmoschus manihot, microfibrous cellulose, furcelleran, fukuronori extracts, macrophomopsis gum, rhamsan gum, levan, okra extracts, seaweed cellulose, kelp extracts, konjac extracts, sweetpotato cellulose, soybean polysaccharide, and nata de coco and solid materials such as polysaccharides, synthetic organic polymers, and silicone type polymers. These materials may be used alone or two or more thereof may be used in combination.

Among these, the raw material composition is more preferably a composition including at least one of gelatin, agar, carrageenan, pectin, glucomannan, pullulan, and sodium alginate.

In addition, as the raw material composition, a solution in which such a material is dissolved in water or an organic solvent may be used.

The raw material composition is preferably a substance that allows a reversible sol-gel transition at a gelation temperature.

The gelation temperature of the raw material composition is 0.5° C. or higher and 65° C. or lower and is preferably 10° C. or higher and 60° C. or lower. Here, the gelation temperature can be measured by the method to be described below in examples.

A device used for adjusting the raw material composition of the present invention can be selected in consideration of a solvent to be used, a raw material composition, or the obtained gel-like composition, and corrosion resistance with respect to a functional gas as long as the object of the present invention is not inhibited. For example, a tank or pot with a stirrer of a material having such corrosion resistance can be used. In addition, when a material of such a device is selected, it is necessary to perform selection in consideration of heat resistance at a usage temperature, and additionally, preventing elution in a gas-containing base material from which a device material component is obtained. For example, device materials such as an SUS material, a glass lining, a fluororesin lining, and a plastic are exemplary examples and the present invention is not limited thereto.

In a specific method of adjusting a raw material composition, when a solvent is used, first, the solvent such as water or an organic solvent at room temperature is put into a dissolution tank, and subsequently, a solid raw material composition (for example, a gelling component) is put thereinto with stirring, the temperature is then raised to a degree at which the solid raw material composition can be dissolved and dissolution is performed and thereby a liquid raw material composition is produced. When no solvent is used, after the solid raw material composition is put into a dissolution tank, the temperature is raised and the solid raw material composition is melted, or a solid raw material composition that is heated and melted in advance may be put into a dissolution tank.

In addition, additives may be appropriately added to the raw material composition. Since additives that can be added to the raw material composition are the same as those described in the gas-containing base material of the present invention, descriptions thereof will be omitted. In particular, at least one of a food additive, a cosmetic additive, an antioxidant, a medium additive, and a feed additive is preferably included.

The functional gas is the same as the functional gas of the above gas-containing base material of the present invention. Examples of the functional gas include hydrogen gas, oxygen gas, nitrogen gas, argon gas, helium gas, carbon dioxide gas, methane gas, ethane gas, propane gas and butane gas and a mixed gas of two or more thereof. Hydrogen gas, oxygen gas, nitrogen gas, argon gas, helium gas, and carbon dioxide gas are preferable, and hydrogen gas is more preferable.

A device used in Process (1) can be selected in consideration of a solvent to be used, a raw material composition, or the obtained gel-like composition, and corrosion resistance with respect to a functional gas as long as the object of the present invention is not inhibited. Any device and instrument used for a known gas and liquid dispersion operation can be used as long as there is provided a method in which an amount of the functional gas which exceeds a saturated solubility when the raw material composition is in a liquid form can be uniformly dispersed as fine bubbles.

For example, when a stirring tank is used, a container such as a pot and a tank including a stirring blade such as a turbine blade or a fullzone blade suitable for gas dispersion in a liquid can be used. When a line mixer is used, a device suitable for finely mixing a gas and a liquid such as a known turbo mixer, static mixer, ejector or the like can be used. When a shaking machine is used, a sealing type shaking machine in which contents are unlikely to leak during shaking can be used.

A preferable aspect of Process (1) is a method in which, while a liquid raw material composition is stirred, a functional gas is supplied to the raw material composition, and the functional gas in the raw material composition is uniformly dispersed as fine bubbles.

As a specific method, when a stirring tank is used, the temperature is maintained at a degree at which the raw material composition is in a liquid form, a functional gas is injected from a lower part of a stirring blade while the liquid raw material composition is stirred, and the functional gas can be finely dispersed in the raw material composition according to stirring.

When a line mixer is used, a liquid raw material composition and a functional gas are injected into a mixer, and the functional gas can be finely dispersed in the raw material composition according to line mixing.

In addition, another preferable aspect of Process (1) is a method in which, without stirring the liquid raw material composition, after a functional gas is supplied to the raw material composition, the functional gas is uniformly dispersed as fine bubbles in the raw material composition according to shaking.

Specifically, when a sealing type shaking machine is used, a volume of a liquid raw material composition which is about ½ of a shaking machine volume is put into a shaking machine, and subsequently, in order to replace a gas phase portion of the shaking machine with a functional gas, a functional gas in an amount 1 to 5 times a gas phase volume of the shaking machine is injected into the liquid raw material composition during bubbling or a gas phase, and the shaking machine is then sealed with a lid. Next, the sealed shaking machine is shaken until the functional gas in a gas phase is finely dispersed in the liquid raw material composition, and the functional gas can be finely dispersed in the raw material composition.

In the production method of the present invention, preferably, the functional gas supplied to the raw material composition becomes fine bubbles with a diameter 1 µm or more and 200 µm or less. When the composition is in a solid form (gel state), if a bubble diameter of the contained functional gas is in a range of 1 µm or more and 200 µm or less, gas bubbles can be uniformly dispersed in the base material. In addition, when gas bubbles are dispersed in the base material, since a rate at which gas bubbles rise due to buoyancy can be reduced, gas bubbles with a high concentration can be incorporated into the base material.

In addition, in the production method of the present invention, regarding the amount of the functional gas supplied to the raw material composition, the amount of the functional gas after Process (3), which is a final product, is preferably in a range of 2 vol % or more and 60 vol % or less and more preferably in a range of 6 vol % or more and 60 vol % or less in terms of volume/weight % (v/w %) in the gel-like composition. When the amount of the functional gas in the composition of the present invention is 2 vol % or more and 60 vol % or less in terms of volume/weight % (v/w %) in the composition of the present invention, gas bubbles with a high concentration can be uniformly and stably retained in the base material. In addition, since a moderate strength for the gas-containing base material can be maintained, it is possible to prevent shape collapse during storage. Here, the amount of the gas is a value obtained by sampling the composition of the present invention under conditions of atmospheric pressure and 10° C. according to a GC analysis method.

Proportions of amounts of the functional gas and the raw material composition prepared may be set appropriately according to the amount of the functional gas in the desired gas-containing base material. In addition, a temperature at which the functional gas is dispersed in the raw material composition may be appropriately set according to the type of the functional gas or the type of the raw material composition depending on the amount of the functional gas in the desired gas-containing base material.

<Process (2)>

Process (2) is a process in which the obtained liquid raw material composition in which fine functional gas bubbles are dispersed is transferred into a filling container and the filling container is filled and sealed. In order to reduce a vaporization loss of the functional gas to the outside of the system, it is preferable to quickly perform filling and sealing as soon as possible.

In particular, the obtained liquid raw material composition in which fine functional gas bubbles are dispersed is gradually cooled, and is preferably transferred into a filling container while the temperature is maintained at a temperature of 5° C. or higher and 20° C. or lower, higher than the gelation temperature of the raw material composition. When the lower limit of the temperature during this transfer is set to a temperature higher than the gelation temperature by 5° C. or higher, it is possible to prevent the viscosity of the base material from becoming a high liquid viscosity of tens of thousands of mPa·s or more, and transfer into the filling container becomes easier. On the other hand, when the temperature is maintained during transfer using a temperature 20° C. higher than the gelation temperature as an upper limit, it is possible to reduce a vaporization loss of the functional gas from the base material. As described above, it is preferable to perform transfer while the temperature when the raw material composition is transferred is maintained in a range of 5° C. or higher and 20° C. or lower than the gelation temperature.

In addition, the viscosity of the liquid raw material composition in which fine functional gas bubbles are dispersed is preferably transferred into a filling container in a range of 100 mPa·s or more and 10,000 mPa·s or less. The viscosity of the raw material composition is preferably 100 mPa·s or more because it is possible to reduce a vaporization loss of the dispersed functional gas to the outside of the system. On the other hand, the viscosity of the raw material composition is preferably 10,000 mPa·s or less because the fluidity suitable for transfer can be secured.

A filling container used is preferably made of a material that does not allow transmission of the functional gas in order to prevent a transmission loss of the functional gas from the material of the filling container. For example, an aluminum pouch, an organic polymer sheet or film through which a functional gas is unlikely to transmit, composite materials thereof, and a metal container are exemplified. The material is not limited to the above exemplary examples of materials as long as a functional gas is unlikely to pass therethrough.

As for a filling method, it is important to fill as much of a gas-containing base material in a liquid form into a filling container as possible such that there is no gas phase space, and quickly seal the filling container in order to prevent vaporization of the functional gas.

A sealing method depends on the type of the filling container. For example, known sealing methods such as heat sealing and a lid with an inner lid may be used.

<Process (3)>

Process (3) is a process in which the obtained raw material composition in which fine functional gas bubbles in a liquid form are dispersed in the sealed filling container is cooled at the gelation temperature or lower of the raw material composition and solidified. According to the process, a gel-like composition containing a functional gas is obtained.

It is preferable to perform cooling as quickly as possible. When the raw material composition in which fine functional gas bubbles in a liquid form are dispersed in the sealed filling container is quickly quenched to the gelation temperature or lower of the gas-containing base material for each filling container, it is possible to minimize a vaporization loss of the functional gas in the gas-containing base material in a liquid form filled into the filling container to the outside of the system.

As long as the filling container into which the base material is filled can be quickly cooled to the gelation temperature or lower, the method thereof is not particularly limited. For example, there are a method in which, after filling and sealing of the base material are completed, each filling container is quickly immersed in a water bath cooled to the gelation temperature or lower of the base material and quenched and a method in which a filling container is cooled in a refrigerant bath in advance, a gas-containing base material in a liquid form is transferred and filled thereinto, and the filling container is sealed.

EXAMPLES

While the present invention will be described below in further detail with reference to examples, the present invention is not limited to any of the following examples unless changing them would change the scope and spirit of the invention.

<Preparation of Raw Material Compositions of Examples 1 to 5>

A raw material composition (gelatin aqueous solution) was produced by the following method using a fish scale-derived gelatin powder and tap water (Kitakyushu City Water Works Bureau).

The gelatin powder and tap water were weighed out into a 1 L resin container with a lid so that a desired gelatin concentration was obtained and the lid was blocked, and the container was left at room temperature, the gelatin was swelled, and then immersed in a hot water bath of 60° C. or higher and 85° C. or lower, the gelatin was dissolved, and thus raw material compositions (gelatin aqueous solutions) with a gelatin concentration of 1, 3, 5, 15, 25, 35, 40, and 50 weight % (wt %) were produced.

<Measurement of Physical Properties>

Next, physical properties of the raw material compositions (gelatin aqueous solutions) were measured.

i) Measurement of Specific Gravity (Volumetric Flask Method)

Figure 1:
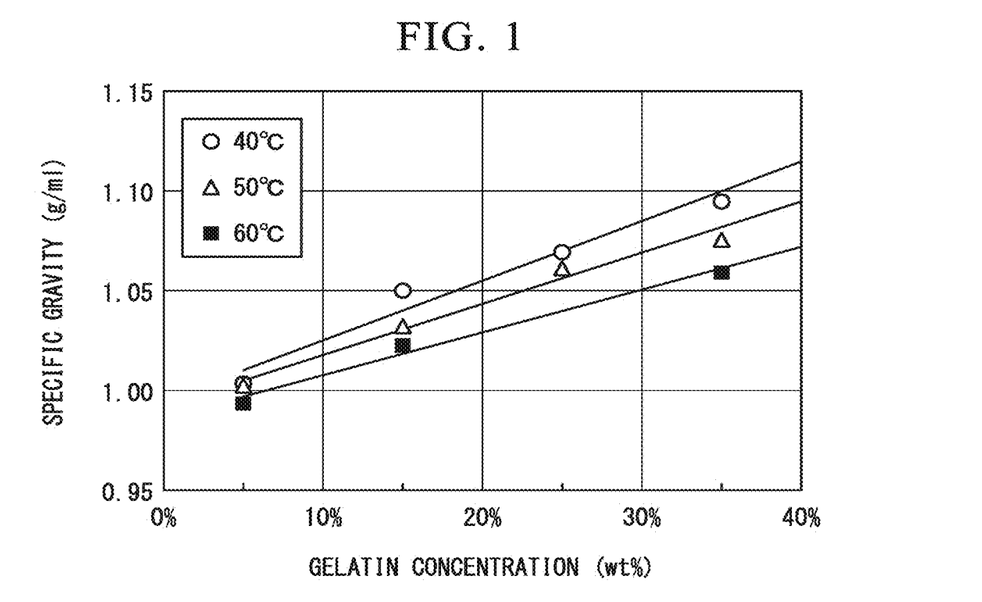
FIG. 1 is a diagram showing specific gravities of raw material compositions (gelatin aqueous solutions) of examples.

Using a 25 ml glass volumetric flask and a constant temperature water tank, a constant volume of pure water was measured at 40, 50, and 60° C. and a pure water density (g/ml) at each temperature was measured. Next, a density of the raw material compositions (gelatin aqueous solutions) was measured according to the same operation and a specific gravity with respect to pure water was obtained. The results are shown in FIG. 1.

ii) Measurement of Gelation Temperature and pH

In order to measure the gelation temperature, 50 ml glass screw bottles were filled about halfway with the raw material compositions (gelatin aqueous solutions) and the bottles were sealed and immersed in a constant temperature water tank, and heated to 75° C.

Next, the temperature at which the raw material composition did not flow even if the screw bottle was tilted at 45° and 90° while the temperature of the constant temperature water tank was gradually reduced was set as a gelation temperature. Here, in order to measure the temperature, a standard mercury thermometer was attached to the outer wall of the screw bottle. The results are shown in Table 1.

TABLE 1

| Gelatin concentration (wt %) | 1% | 3% | 5% | 15% | 25% | 35% | 50% |
|---|---|---|---|---|---|---|---|
| Gelation temperature (° C.) | 0.5 | 13 | 16 | 20 | 22 | 26 | 27 |

In addition, using a pH meter (D-51) (commercially available from Horiba Ltd.), a calibration operation was performed at 25° C. using pH standard solutions 4.01, 6.86, 9.18, and a pH of the raw material compositions (gelatin aqueous solutions) was then measured at the same temperature. The pH was about 6.

iii) Measurement of Viscosity

Figure 2:
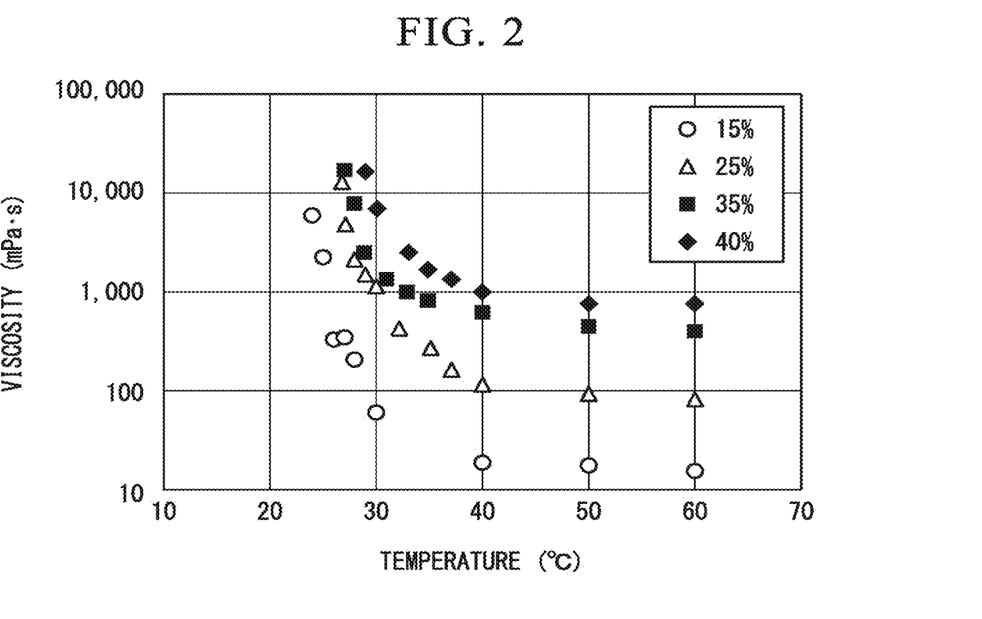
FIG. 2 is a diagram showing viscosities of raw material compositions (gelatin aqueous solutions) of examples.

In order to measure the viscosity, using an E type viscometer (RE-105L for low viscosity, RE-215U for high viscosity) (commercially available from Toki Sangyo Co., Ltd.), a viscosity of the raw material compositions (gelatin aqueous solutions) was measured. The results are shown in FIG. 2.

<Example 1> Production of "High-Concentration Hydrogen Gas-Containing Base Material-1"

A functional gas dispersion device including a fullzone type stirring blade, a thermometer, a gas inlet pipe (a gas outlet was fixed to a lower part of a stirring blade), and a Liebig condenser in a 1 L glass separable flask with a jacket was used. Here, the functional gas was injected into the device via an area type flow meter, and the temperature was controlled by circulating water whose temperature was controlled into the jacket from a constant temperature water tank.

Process (1a)

In the same manner as in the above <Preparation of raw material compositions of Examples 1 to 5>, "a raw material composition (gelatin aqueous solution) with a gelatin concentration of 35 wt %" was produced. 500 g of the "raw material composition (gelatin aqueous solution) with a gelatin concentration of 35 wt %" was put into the device. After the internal temperature was raised to 70° C. and maintained with stirring, while hydrogen gas was injected at 20 mL/min from a lower part of the stirring blade and dispersed as fine bubbles in a retaining material, when a liquid surface rose to about 1.7 times the height of the liquid surface during preparation, introduction of hydrogen gas was stopped, and hydrogen was uniformly dispersed as fine bubbles in the raw material composition.

Process (2a)

The raw material composition in which hydrogen gas was dispersed as fine bubbles was cooled until the internal temperature reached 32° C. and was put into an aluminum pouch at the same temperature, and the aluminum pouch was filled and sealed.

Process (3a)

The aluminum pouch was immediately immersed in water at 5° C., and cooled and solidified to obtain a gel-like composition containing hydrogen gas (a "high-concentration hydrogen gas-containing base material-1").

<Evaluation>

(1) Measurement of Content of Hydrogen in "High-Concentration Hydrogen Gas-Containing Base Material-1"

(Specific Gravity Method)

100 ml of an extracted solution at 32° C. was directly put into a 100 ml measuring cylinder, and immediately immersed in cold water at 5 to 10° C., and gelling was caused. The weight/volume thereof was measured and a specific gravity was measured as 0.66 g/ml. From a specific gravity difference from the raw material composition before hydrogen gas was dispersed, when the amount of hydrogen gas in the high-concentration hydrogen gas-containing base material was obtained by the following calculation formula of the specific gravity method, the result indicated 40 vol % (v/w %) and that hydrogen gas was included at a high concentration.

<Calculation Formula of Specific Gravity Method>

---

The concentration (vol %) of hydrogen in high-concentration hydrogen gas-containing base material = (specific gravity of raw material composition before gas is dispersed = specific gravity of composition after gas is dispersed)/specific gravity of raw material composition before gas is dispersed × 100 = (1.10 − 0.66)/1.10 × 100 = 40 vol %

---

(GC Analysis Method)

In addition, the "high-concentration hydrogen gas-containing base material-1" was sampled at 10° C., and was accurately weighed out into a sample bottle for headspace GC analysis used for gas chromatographic analysis (hereinafter referred to as GC analysis) and the bottle was sealed. Then, heating and dissolving were performed in a constant temperature water tank at 70° C. until a transparent liquid form without containing bubbles was obtained and hydrogen gas in a gas phase was released. Next, according to a method in which a gas (gas phase) was sampled in a sample bottle, and hydrogen gas was quantified by GC analysis (TCD detector), when the amount of hydrogen gas in the "high-concentration hydrogen gas-containing base material-1" was measured, the result indicated 36 vol % (v/w %) and that hydrogen gas was included at a high concentration.

In addition, based on the above results, it was confirmed that contents of hydrogen gas obtained by a specific gravity method and a GC analysis method were substantially the same numerical value.

(2) Observation Results Before and after Hydrogen Gas Dispersion

Figure 3:
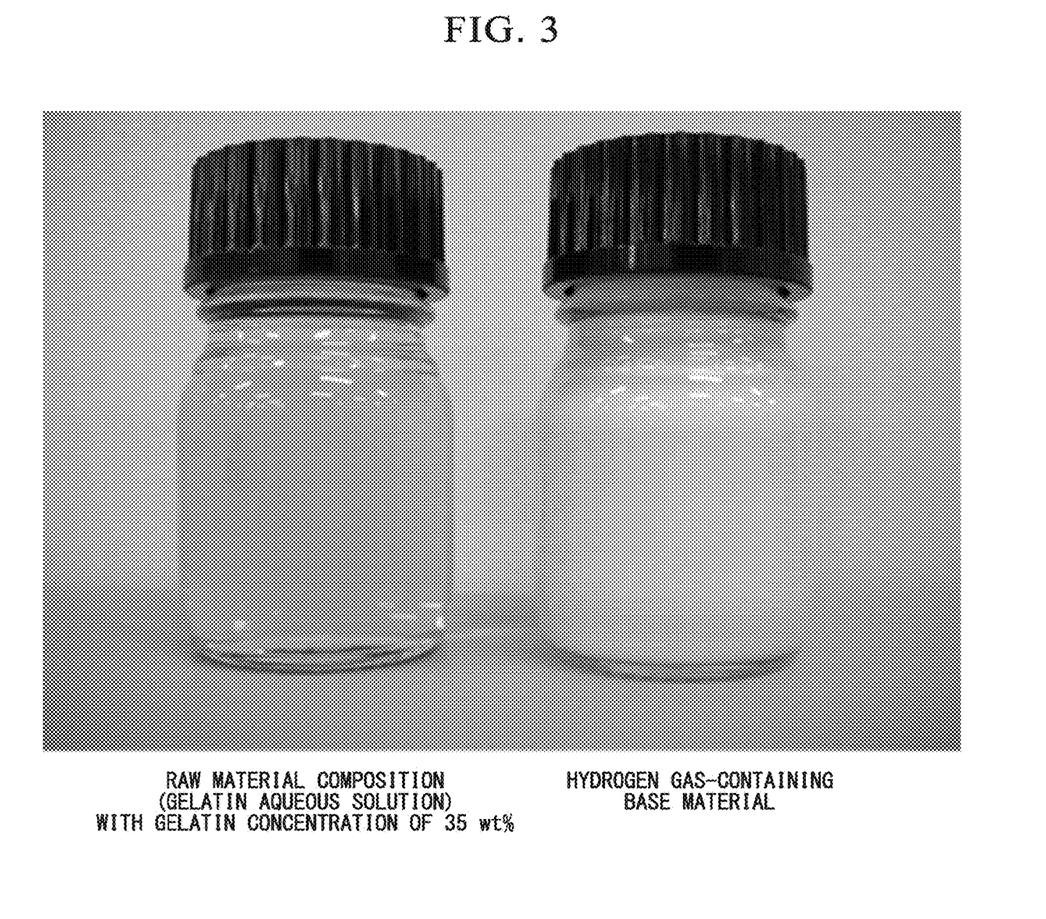
FIG. 3 is an appearance photo of a raw material composition (gelatin aqueous solution) having a gelatin concentration of 35 wt % and a high-concentration hydrogen gas-containing base material-1 of Example 1.

FIG. 3 shows an appearance photo of a "raw material composition (gelatin aqueous solution) with a gelatin concentration of 35 wt %," and a "high-concentration hydrogen gas-containing base material-1" in which hydrogen gas was dispersed in the form of fine bubbles to the raw material composition at 10° C.

From the appearance photo in FIG. 3, while "a raw material composition (gelatin aqueous solution) with a gelatin concentration of 35 wt %" was transparent, the "high-concentration hydrogen gas-containing base material-1" in which hydrogen gas was finely dispersed at a high concentration was white opaque because fine hydrogen bubbles with a micrometer size were dispersed at a high concentration.

In addition, in order to observe a dispersion state of hydrogen gas bubbles in "high-concentration hydrogen gas-containing base material-1," the base material was cut with a sharp knife, and a cross section thereof was observed in a reflected image from a surface layer to a depth of about 200 μm under a microscope (digital microscope VHX-900F commercially available from Keyence Corporation). The results are shown in FIG. 4 and FIG. 5.

Figure 4:
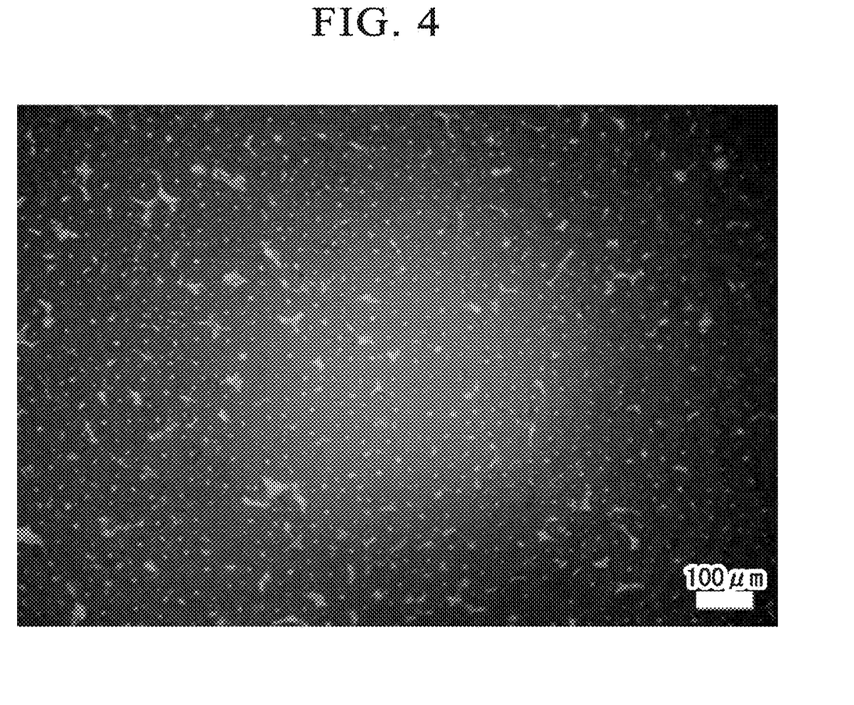
FIG. 4 is a cross section photo (a microscope magnification of 100) of the high-concentration hydrogen gas-containing base material-1 of Example 1.
Figure 5:
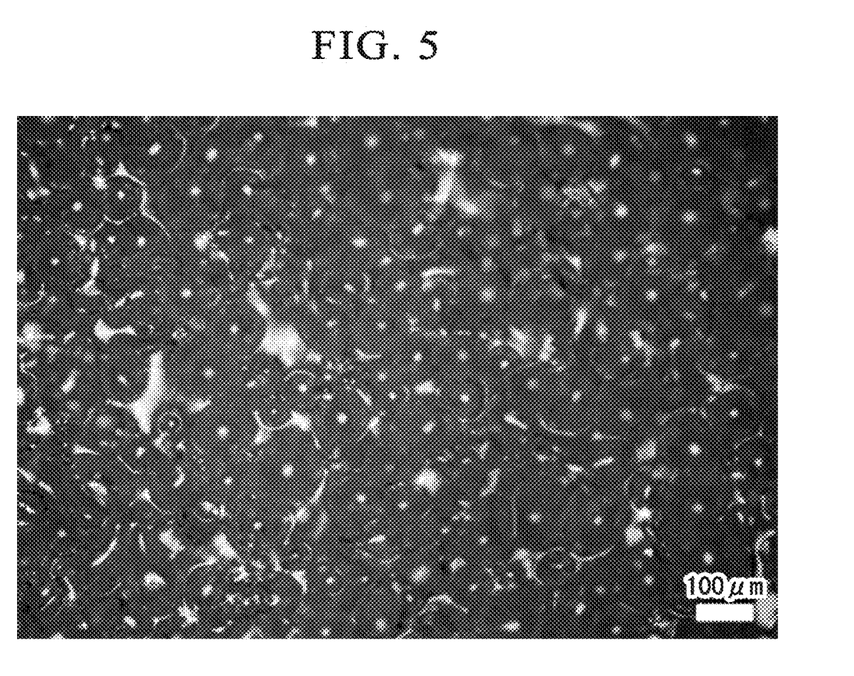
FIG. 5 is a cross section photo (a microscope magnification of 200) of the high-concentration hydrogen gas-containing base material-1 of Example 1.

It was confirmed from microscope observation of a cross section of the "high-concentration hydrogen gas-containing base material-1" in FIG. 4 and FIG. 5 that fine bubbles with a bubble diameter of 1 μm or more and 200 μm or less were dispersed at a high concentration.

<Example 2> Process of Producing "High-Concentration Hydrogen Gas-Containing Base Material-2" (1b)

In the same manner as in the above <Preparation of raw material compositions of Examples 1 to 5>, a "raw material composition (gelatin aqueous solution) with a gelatin concentration of 35 wt %" was produced. 500 g of "the raw material composition with a gelatin concentration of 35 wt %) (gelatin aqueous solution)" was put into a 1 L polyethylene container with a lid, the container was immersed in a constant temperature water tank at 70° C., and the temperature was raised and maintained. Then, bubbles on the surface (gas phase interface) of the raw material composition rose to a mouth of the container while bubbling of hydrogen gas was generated on a bottom of the container at 100 mL/min, and thus blowing of hydrogen gas was stopped and sealing was performed. The sealed container was removed from the constant temperature water tank, rapid shaking by hand gesture at room temperature continued until the internal temperature reached 35° C., and hydrogen gas was finely dispersed in the raw material composition.

Process (2b)

The raw material composition in which hydrogen gas was dispersed as fine bubbles was put into an aluminum pouch at 30 to 35° C. and the aluminum pouch was filled and sealed.

Process (3b)

The aluminum pouch was immediately immersed in water at 5° C., cooled and solidified to obtain a "high-concentration hydrogen gas-containing base material-2."

<Evaluation>

(1) Measurement of Hydrogen Content of "High-Concentration Hydrogen Gas-Containing Base Material-2"

The amount of hydrogen gas in the "high-concentration hydrogen gas-containing base material-2" was measured in the same manner as in Example 1 according to a GC analysis method, and the result was 28 vol %.

(2) Storage Stability of "High-Concentration Hydrogen Gas-Containing Base Material-2"

The "high-concentration hydrogen gas-containing base material-2" was stored in a refrigerator at 5 to 10° C., and a change in the amount of hydrogen gas over time was measured after 48 days according to a GC analysis method. The result was 26 vol %. Based on the result, it was confirmed that a retention amount of hydrogen gas in the base material hardly changed.

<Example 3> Production of "High-Concentration Hydrogen Gas-Containing Base Material-3"

A "high-concentration hydrogen gas-containing base material-3" was produced in the same manner as in Example 1 except that the raw material composition used in Example 1 was changed from a "raw material composition (gelatin aqueous solution) with a gelatin concentration of 35 wt %" to a "raw material composition (gelatin aqueous solution) with a gelatin concentration of 25 wt %."

When the amount of hydrogen gas in the "high-concentration hydrogen gas-containing base material-3" was measured, the result indicated 53 vol % (a specific gravity before hydrogen gas was dispersed was 1.07, and a specific gravity after hydrogen gas was dispersed was 0.50) according to a specific gravity method and that hydrogen gas was included at a high concentration.

<Example 4> Production of "High-Concentration Hydrogen Gas-Containing Base Material-4"

A "high-concentration hydrogen gas-containing base material-4" was produced in the same manner as in Example 2 except that the raw material composition used in Example 1 was changed from a "raw material composition (gelatin aqueous solution) with a gelatin concentration of 35 wt %" to a "raw material composition (gelatin aqueous solution) with a gelatin concentration of 40 wt %."

When the amount of hydrogen gas in the "high-concentration hydrogen gas-containing base material-4" was measured, the result indicated 29 vol % (a specific gravity before hydrogen gas was dispersed was 1.12, and a specific gravity after hydrogen gas was dispersed was 0.80) according to a specific gravity method and 27 vol % according to a GC method, and that hydrogen gas was included at a high concentration.

<Example 5> Production of "High-Concentration Air-Containing Base Material-5"

A "high-concentration air-containing base material-5" was produced in the same manner as in Example 2 except that the functional gas in Example 1 was changed from "hydrogen gas" to "air."

When the amount of air in the "high-concentration air-containing base material-5" was measured according to a specific gravity method, the result indicated 35 vol % (a specific gravity before air was dispersed was 1.10, and the specific gravity after air was dispersed was 0.72), and that air was included at a high concentration.

Figure 6:
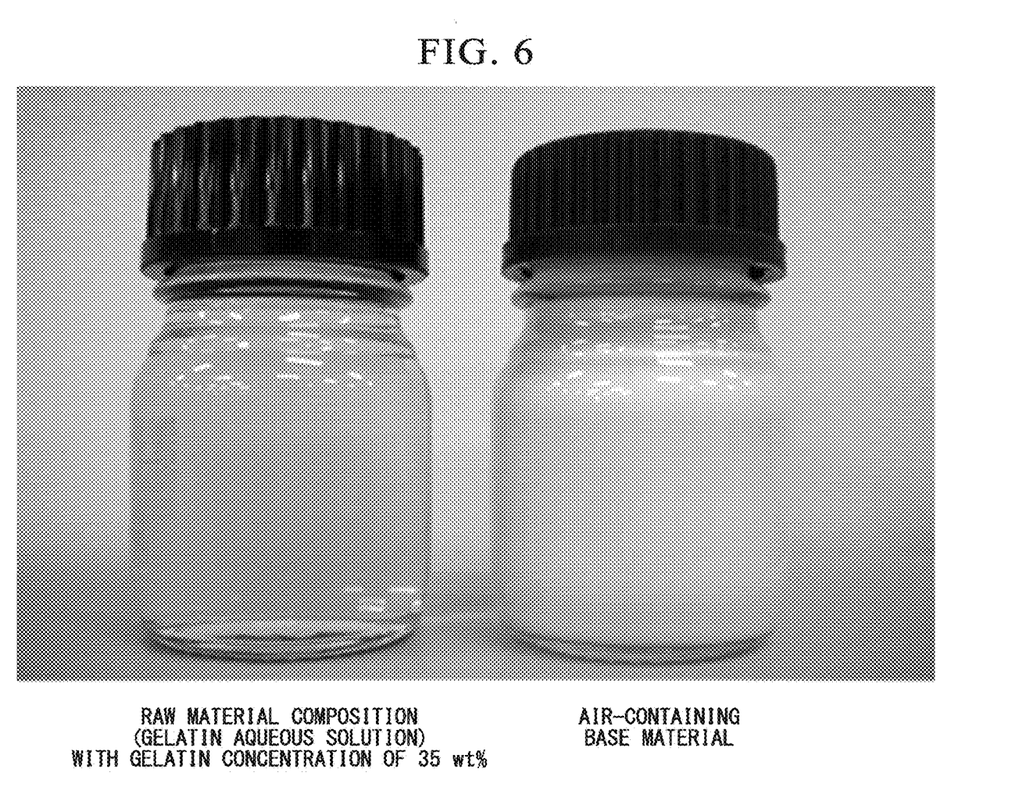
FIG. 6 is an appearance photo of a raw material composition (gelatin aqueous solution) having a gelatin concentration of 35 wt % and a high-concentration air-containing base material-5 of Example 5.

In addition, FIG. 6 shows an appearance photo of a "raw material composition (gelatin aqueous solution) with a gelatin concentration of 35 wt %" and a "high-concentration air-containing base material" in which air was dispersed in the form of fine bubbles in the raw material composition at 10° C.

<Preparation of Raw Material Compositions of Examples 6 to 11>

Components in Table 2 were weighed out into a 1 L resin container with a lid, and the lid was blocked, and the container was left at room temperature and a solid component was swelled, and then immersed in a hot water bath at 60 to 95° C., the solid component was dissolved, and thus raw material compositions were produced. A gelation temperature was measured according to the above description in "ii) measurement of gelation temperature and pH." The results are shown in Table 3.

TABLE 2

| | Unit: wt % | | | | | |
|---|---|---|---|---|---|---|
| Names of raw materials | Example 6 | Example 7 | Example 8 | Example 9 | Example 10 | Example 11 |
| Gelatin (fish scale-derived gelatin and crushed granular form) | — | 15 | — | 15 | — | 10 |
| Agar (derived from *Gracilaria vermiculophylla* and powdery) | 6 | 6 | — | — | — | — |
| Carrageenan (k (Kappa) type, content of sulfate group of 20 to 30 wt %) | — | — | 3.5 | 2.5 | — | — |
| HM pectin (derived from apple, and content of methoxyl group of 7 wt % or more) | — | — | — | — | 3 | 2.5 |
| Granulated sugar (derived from sugarcane) | — | — | — | — | 60 | 30 |

TABLE 2-continued

Unit: wt %

| Names of raw materials | Example 6 | Example 7 | Example 8 | Example 9 | Example 10 | Example 11 |
|---|---|---|---|---|---|---|
| Citric acid for addition to foods commercially available from Kanto Chemical Co., Inc. | — | — | — | — | — | 3 |
| Tap water (Kitakyushu City Water Works Bureau) | The remainder | The remainder | The remainder | The remainder | The remainder | The remainder |

TABLE 3

| | Example 6 | Example 7 | Example 8 | Example 9 | Example 10 | Example 11 |
|---|---|---|---|---|---|---|
| Gelation temperature (° C.) | 43° C. | 22° C. | 42° C. | 44° C. | None | 29° C. |

<Example 6> Production of "High-Concentration Hydrogen Gas-Containing Base Material-6"

Process (1c)

Hydrogen gas was uniformly dispersed as fine bubbles in a raw material composition in the same manner as in Example 1 except that the raw material composition used in Example 1 was changed from a "raw material composition (gelatin aqueous solution) with a gelatin concentration of 35 wt %" to "a raw material composition (agar aqueous solution) of Example 6 in Table 2."

Process (2c)

The raw material composition in which hydrogen gas was dispersed as fine bubbles was put into an aluminum pouch and the aluminum pouch was filled and sealed.

Process (3c)

The aluminum pouch was immediately immersed in water at 5° C. and cooled and solidified to obtain a gel-like composition containing hydrogen gas ("high-concentration hydrogen gas-containing base material-6").

<Evaluation>

(1) Measurement of Hydrogen Content of "High-Concentration Hydrogen Gas-Containing Base Material-6"

When the amount of hydrogen gas in the "high-concentration hydrogen gas-containing base material-6" was measured in the same manner as in Example 1 according to a GC analysis method, the result indicated 7.3 vol % and that hydrogen gas was included at a high concentration.

<Example 7> Production of "High-Concentration Hydrogen Gas-Containing Base Material-7"

A "high-concentration hydrogen gas-containing base material-7" was produced in the same manner as in Example 1 except that the raw material composition used in Example 1 was changed from a "raw material composition (gelatin aqueous solution) with a gelatin concentration of 35 wt %" to "a raw material composition (gelatin and agar aqueous solution) of Example 7 in Table 2."

When the amount of hydrogen gas in the "high-concentration hydrogen gas-containing base material-7" was measured, the result indicated 10.0 vol % according to GC method and that hydrogen gas was included at a high concentration.

<Example 8> Production of "High-Concentration Hydrogen Gas-Containing Base Material-8"

A "high-concentration hydrogen gas-containing base material-8" was produced in the same manner as in Example 1 except that the raw material composition used in Example 1 was changed from a "raw material composition (gelatin aqueous solution) with a gelatin concentration of 35 wt %" to a "raw material composition (carrageenan aqueous solution) of Example 8 in Table 2."

When the amount of hydrogen gas in the "high-concentration hydrogen gas-containing base material-8" was measured, the result indicated 6.3 vol % according to a GC method and that hydrogen gas was included at a high concentration.

<Example 9> Production of "High-Concentration Hydrogen Gas-Containing Base Material-9"

A "high-concentration hydrogen gas-containing base material-9" was produced in the same manner as in Example 1 except that the raw material composition used in Example 1 was changed from a "raw material composition (gelatin aqueous solution) with a gelatin concentration of 35 wt %" to "a raw material composition (gelatin and carrageenan aqueous solution) of Example 9 in Table 2."

When the amount of hydrogen gas in the "high-concentration hydrogen gas-containing base material-9" was measured, the result indicated 19.0 vol % according to a GC method and that hydrogen gas was included at a high concentration.

<Example 10> Production of "High-Concentration Hydrogen Gas-Containing Base Material-10"

A "high-concentration hydrogen gas-containing base material-10" was produced in the same manner as in Example 1 except that the raw material composition used in Example 1 was changed from a "raw material composition (gelatin aqueous solution) with a gelatin concentration of 35 wt %" to a "raw material composition (HM pectin and granulated sugar solution) of Example 10 in Table 2."

When the amount of hydrogen gas in the "high-concentration hydrogen gas-containing base material-10" was measured, the result indicated 6.7 vol % according to a GC method and that hydrogen gas was included at a high concentration.

<Example 11> Production of "High-Concentration Hydrogen Gas-Containing Base Material-11"

A "high-concentration hydrogen gas-containing base material-11" was produced in the same manner as in Example 1 except that the raw material composition used in Example 1 was changed from a "raw material composition (gelatin aqueous solution) with a gelatin concentration of 35 wt %" to a "raw material composition (gelatin, HM pectin, granulated sugar, and a citric acid aqueous solution) of Example 11 in Table 2."

When the amount of hydrogen gas in the "high-concentration hydrogen gas-containing base material-11" was measured, the result indicated 17.0 vol % according to a GC method and that hydrogen gas was included at a high concentration.

<Reference Example>: Amount of Saturated Dissolved Hydrogen in Nanobubble Hydrogen Water A method of producing a functional jelly using hydrogen nanobubbles is described in Patent Document 2 (Japanese Patent No. 4450863). In the method, hydrogen nanobubbles are generated in water or a low viscosity liquid and transferred to another tank, and a gelling agent is added thereto to cause gelling, and thereby a functional jelly is obtained. However, the concentration of hydrogen in hydrogen nanobubble water and the concentration of hydrogen in a functional jelly product are not described and are unknown. Therefore, the inventors conducted the following verification in order to obtain a saturated concentration of hydrogen nanobubbles in water.

Figure 7:
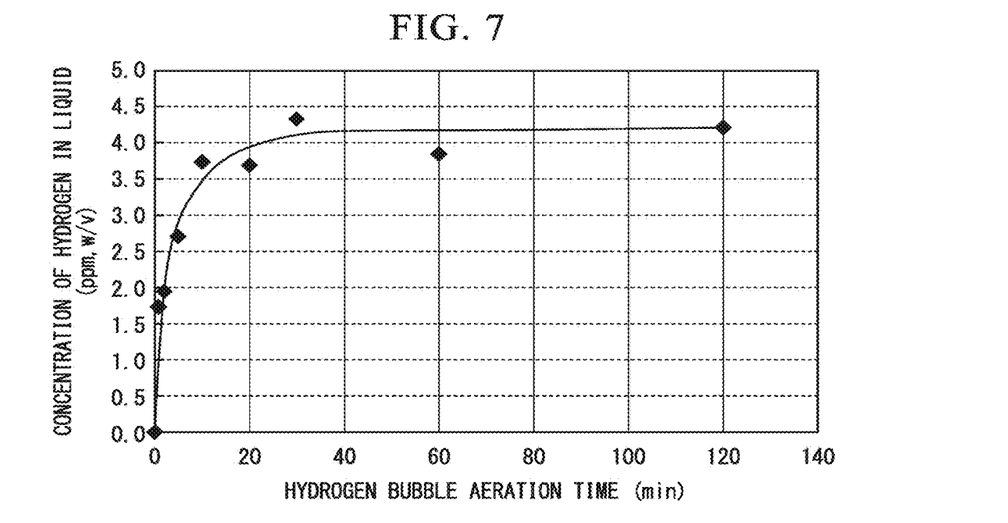
FIG. 7 is a diagram showing a concentration of hydrogen in nanobubble hydrogen water of a reference example.

500 ml of ultra pure water was put into a 500 ml glass bottle, and this and a nano valve generating device (ultra fine bubble generating device: AMB3 type commercially available from Asupu Co., Ltd.) were subjected to pump circulation, hydrogen gas was injected into the nanobubble generating device, and pump circulation continued while hydrogen nanobubbles were generated. Circulating water was sampled over time and an amount of nanobubble hydrogen in ultra pure water was measured by a gas chromatographic analysis method. Here, in the nanobubble generating device, since hydrogen microbubbles were also mixed and water became cloudy, a sampling solution was left for several minutes, a transparent liquid in which hydrogen microbubbles were gas phase-vaporized was injected as nanobubble hydrogen water into a GC analysis machine, and measurement was performed. The results are shown in FIG. 7.

It was found that the amount of hydrogen nanobubbles in water reached a saturation retention amount about 30 minutes after injection of hydrogen nanobubbles into ultra pure water started and the concentration thereof was about 4.2 ppm (w/v).

The concentration was "4.9 vol % at 10° C." in terms of volume/weight % (vol %), and was a much lower level than a content in the case of hydrogen gas in a high concentration functional-gas-containing base material of the present invention.

INDUSTRIAL APPLICABILITY

Since the gas-containing base material of the present invention can retain a functional gas at a high concentration, it can be applied to various applications such as foods, cosmetics, medicine, and cell culture.

What is claimed is:

1. A gas-containing base material comprising a composition comprising hydrogen gas,
    wherein the composition is a gel composition having a gelation temperature in a range of 0.5° C. or higher and 65° C. or lower at which a liquid form is able to be changed to a solid form by cooling,
    wherein the composition comprises an amount of a bubble state hydrogen gas which exceeds a saturated solubility when the composition is in a liquid form, and
    wherein an amount of the hydrogen gas is 10 to 60 vol % in terms of volume/weight % (v/w %) of the composition,
    wherein the composition farther comprises gelatin and at least one selected from the group consisting of carrageenan, pectin, glucomannan, pullulan, and sodium alginate, wherein the amount of hydrogen gas in the base material remains substantially unchanged after 48 days at 5-10° C.

2. The gas-containing base material according to claim 1, wherein, when the composition is in a solid form, a bubble diameter of the contained hydrogen gas is in a range of 1 μm or more and 200 μm or less.

3. The gas-containing base material according to claim 1, wherein a gelation temperature of the composition is 10° C. or higher and 60° C. or lower.

4. The gas-containing base material according to claim 1, wherein the composition comprises an additive.

* * * * *